(12) United States Patent
Guo et al.

(10) Patent No.: US 8,610,073 B2
(45) Date of Patent: Dec. 17, 2013

(54) MONOCHROMATIC WAVELENGTH VARIABLE TERAHERTZ WAVE GENERATION/DETECTION SYSTEM AND METHOD

(75) Inventors: Ruixiang Guo, Saitama (JP); Hiroaki Minamide, Saitama (JP); Hiromasa Ito, Saitama (JP)

(73) Assignee: Riken, Saitama (JP)

( * ) Notice: Subject to any disclaimer, the term of this patent is extended or adjusted under 35 U.S.C. 154(b) by 762 days.

(21) Appl. No.: 12/874,912

(22) Filed: Sep. 2, 2010

(65) Prior Publication Data

US 2011/0057109 A1    Mar. 10, 2011

(30) Foreign Application Priority Data

Sep. 3, 2009  (JP) ................................. 2009-203791
Sep. 17, 2009 (JP) ................................. 2009-215694

(51) Int. Cl.
G01J 5/02    (2006.01)
G01J 5/00    (2006.01)
G01J 3/28    (2006.01)

(52) U.S. Cl.
USPC .......................... 250/340; 250/338.1; 359/326

(58) Field of Classification Search
USPC ..................... 250/340, 338.1, 341.1; 359/326
See application file for complete search history.

(56) References Cited

U.S. PATENT DOCUMENTS 7,531,803 B2 *  5/2009  Mittleman et al. .......... 250/341.1
7,782,909 B2 *  8/2010  Oh et al. ........................ 372/4

2002/0024718 A1   2/2002  Kawase et al.
2003/0227668 A1  12/2003  Imai et al.
2009/0251767 A1  10/2009  Ikari et al.

FOREIGN PATENT DOCUMENTS

JP    2002-72269 A    3/2002
JP    2003-005238 A   1/2003
JP    2003-302666 Q   10/2003
JP    2006-163026 A   6/2006

OTHER PUBLICATIONS

A. A. Babin et al., "Use of Stimulated Scattering by Polaritons in Detection of Submillimeter Radiation," Sov. J. Quantum Electron, Jul. 1983, pp. 958-960, vol. 13, No. 7.
Yujie J. Ding et al., "Efficient THz Generation and Frequency Upconversion in GaP Crystals," Solid-State Electronics 50, 2006, pp. 1128-1136.
Ruixiang Guo, et al., "High Sensitive Coherent Detection of Terahertz Waves at Room Temperature using a Parametric Process," Applied Physics Letters, 021106, Jul. 15, 2008, vol. 93.

* cited by examiner

Primary Examiner — David Porta
Assistant Examiner — Faye Boosalis
(74) Attorney, Agent, or Firm — Sughrue Mion, PLLC

(57) ABSTRACT

To provide a monochromatic wavelength variable terahertz wave generation/detection system that has high detection sensitivity at room temperature and that can quickly operate at the same time, excitation light of monochromatic wavelength generated from one excitation light source is inputted to a wavelength variable terahertz wave source and a nonlinear light conversion terahertz wave detector through an excitation light phase control optical system shown below. The excitation light phase control optical system includes, on a light path of the excitation light, an optical element capable of simultaneously changing an incidence angle of the excitation light to a generation point of a terahertz wave in the wavelength variable terahertz wave source and an incidence angle of the excitation light to an incidence point of the terahertz wave in the nonlinear light conversion terahertz wave detector to set both the generation point and the incidence point at the same time on the focal points in a confocal optical system.

11 Claims, 13 Drawing Sheets

A

B f: Focal distance

A f : Focal distance

B f : Focal distance

A

B

MONOCHROMATIC WAVELENGTH VARIABLE TERAHERTZ WAVE GENERATION/DETECTION SYSTEM AND METHOD

BACKGROUND OF THE INVENTION

1. Field of the Invention

The present invention relates to a monochromatic wavelength variable terahertz wave generation/detection system and a method capable of satisfying angle phase matching conditions at the same time in both generation and detection of a terahertz wave, and particularly, to a monochromatic wavelength variable terahertz wave generation/detection system and a method capable of operating at room temperature while being capable of a high-sensitivity and fast operation. In the specification, a terahertz wave denotes a wave at about 0.1 to 100 THz frequency.

2. Background Art

In recent years, technical development in the terahertz wave area is expanding on a daily basis. Accordingly, studies on applications of a terahertz wave are extending to fields from basic science to industrial inspection (fields such as diagnostic apparatus, product inspection apparatus, forgery prevention apparatus, and personal belonging inspection apparatus). Conventionally, a terahertz time-domain spectrometer is mainly used as a terahertz wave generation/detection system. The terahertz time-domain spectrometer measures, on a time axis, a broadband terahertz wave generated by directing a femtosecond laser to a photoconductive element (PC antenna) and applies Fourier transform to the measurement result to convert the measurement result to information on a frequency axis.

DOCUMENT LIST

Patent Document

Patent Document 1: JP Patent Publication (Kokai) No. 2003-005238 A
Patent Document 2: JP Patent Publication (Kokai) No. 2002-072269 A
Patent Document 3: JP Patent Publication (Kokai) No. 2003-302666 A
Patent Document 4: JP Patent Publication (Kokai) No. 2006-163026 A Non Patent Document Non Patent Document 1: A. A. Babin, V. N. Petryakov, and G. I. Freidman, "Use of stimulated scattering by polaritons in detection of submillimeter radiation," Soviet Journal of Quantum Electronics 13, 958-960 (1983).
Non Patent Document 2: Y. J. Ding, and W. Shi, "Efficient THz generation and frequency upconversion in GaP crystals," Solid-State Electronics 50, 1128-1136 (2006).
Non Patent Document 3: R. Guo, S. Ohno, H. Minamide, T. Ikari, and H. Ito, "Highly sensitive coherent detection of terahertz waves at room temperature using a parametric process," Appl. Phys. Lett. 93, 021106 (2008).

However, a terahertz wave of monochromatic wavelength is expected to be used in the terahertz wave generation/detection system in the near future, and a method of directly changing and using the frequency (wavelength) is expected to become important. The terahertz wave of monochromatic wavelength denotes a terahertz wave, the spectral width of which is narrowed down.

However, when a terahertz wave source capable of changing the wavelength in a wide band (hereinafter called "broadband wavelength variable terahertz wave source") or a monochromatic light source, such as a terahertz wave quantum cascade laser, is used to generate the terahertz wave, there is a problem that there is no terahertz wave detector capable of efficiently and quickly detecting the terahertz wave at room temperature through a wide frequency range.

Hereinafter, features and problems of currently available techniques will be described.

(Terahertz Time-Domain Spectrometer)

A terahertz time-domain spectrometer uses a femtosecond laser as a terahertz wave source. The femtosecond laser is directed to a gap of a DC-biased photoconductive antenna to instantaneously short-circuit the gap. The short circuit generates a broadband terahertz wave in the photoconductive antenna. Meanwhile, another photoconductive antenna is used to detect the broadband terahertz wave. In this case, the electric field intensity of the broadband terahertz wave is applied as a bias to the gap of the photoconductive antenna, and the femtosecond laser measures the time waveform as a sample. The terahertz time-domain spectrometer applies Fourier transform to the measured sampling data, and information is formed as a frequency spectrum.

(Terahertz Detector Capable of Measuring Terahertz Wave of Monochromatic Wavelength)

Meanwhile, an example of a terahertz wave detector capable of measuring a terahertz wave of monochromatic wavelength, etc. includes the following.

(Thermal-Detection Terahertz Wave Detector)

This type of detector uses, for example, a bolometer, a pyroelectric element, and a Golay cell as thermal detection elements. A detector, such as a silicon bolometer, that operates at extremely low temperature (for example, 4 k) has relatively high detection sensitivity. However, liquid helium needs to be used, and there is a problem that the detector cannot be generally used. Meanwhile, a detector that uses a pyroelectric element or a Golay cell operates at normal temperature. However, the detection sensitivity is worse than that of the bolometer by more than double digits. In addition, high output of a terahertz wave source is not easy, and the detector often poses a problem in use. The response speed of this type of detector is basically slow, from microseconds to milliseconds. There is a problem that the detector cannot be used in advanced measurement, such as time-resolved spectroscopy.

(Terahertz Square-Law Detector)

This type of detector uses, for example, a Schottky diode as a detection element. A detector that uses a GaAs semiconductor, etc. capable of fast operation can operate at room temperature and is also capable of pulse measurement in a shorter time than a nanosecond. However, the detector is configured to detect the terahertz wave through an antenna, and there is a problem that the detection performance depends on the antenna performance. Moreover, the antenna is designed to be optimal at a specific frequency range, and the antenna cannot highly efficiently detect the terahertz wave throughout a wide band (for example, 1 to 3 THz). The wavelength of the terahertz wave is less than several hundred μm, which is shorter than the microwave, etc. Therefore, the detection output is reduced according to the wavelength, and an error during production of the antenna significantly affects the detection performance.

A whisker antenna is used for the Schottky diode capable of responding up to high frequencies. In that case, a needle-shaped antenna is brought into contact with the detector for use. However, the antenna and the detector may be separated by a mechanical impact (such as vibration), and the structure has a problem for stably measuring the terahertz wave.
(Quantum Detector)

Examples of this type of detector include a quantum dot detector and a semiconductor photoconductive detector. The sensitivity of the quantum detector is excellent, and the response speed is fast. On the other hand, the operation temperature is at extremely low temperature. Therefore, the detector is not generally used, and the detector is applicable only in limited fields, such as astronomy, in which ultimate performance is required.

SUMMARY OF THE INVENTION

As a result of analyzing the problems, the present inventors propose a monochromatic wavelength variable terahertz wave generation/detection system and a method with high detection sensitivity at room temperature and capable of fast operation at the same time. Consequently, in the present invention, excitation light of monochromatic wavelength generated from one excitation light source enters a wavelength variable terahertz wave source and a nonlinear conversion terahertz wave detector through an excitation light phase control optical system shown below. The excitation light phase control optical system includes, on a light path of the excitation light, an optical element capable of simultaneously changing an incidence angle of the excitation light to a generation point and an incidence angle of the excitation light to an incidence point to set both the generation point of a terahertz wave in the wavelength variable terahertz wave source and the incidence point of the terahertz wave in the nonlinear light conversion terahertz wave detector on the focal points in the confocal optical system at the same time.

Excitation light generated from one excitation light source is used to generate and detect a terahertz wave. Therefore, the coherence between the excitation light and the terahertz wave at the generation point and the detection point (incidence point) of the terahertz wave can be increased. Furthermore, the terahertz wave can be varied in a wide band while simultaneously satisfying angle phase matching conditions in the wavelength variable terahertz wave source and the nonlinear light conversion terahertz wave detector. Moreover, an optical element capable of fast operation at room temperature can be used for the confocal optical system. As a result, according to the present invention, a monochromatic wavelength variable terahertz wave generation/detection technique with high detection sensitivity at room temperature and capable of fast operation at the same time can be realized.

DESCRIPTION OF SYMBOLS $101a$, $101b$ terahertz wave generation/detection systems, 103 excitation light source, 105 wavelength variable terahertz wave source, 107, $107a$, $107b$ excitation light phase control optical systems, 109 nonlinear light conversion terahertz wave detector, 111 terahertz wave phase control optical system, 113 light detector, 115 control apparatus, 117 display apparatus, 121 nonlinear optical crystal, 122, 123 resonator mirrors, 132 mirror arranged on galvano scanner, 151 nonlinear optical crystal, 161, 163 parabolic mirrors, P1 generation point, P2 incidence point.

DETAILED DESCRIPTION OF THE PREFERRED EMBODIMENTS

Hereinafter, an embodiment of the present invention will be described based on the drawings. Configurations of apparatuses and processing operations described below are examples, and combinations of the embodiment and known techniques as well as replacements of the embodiment can realize other embodiments.
(A) Angle Phase Matching Conditions The embodiment shown below describes a terahertz wave generation/detection system that simultaneously realizes generation and detection of a terahertz wave by causing excitation light to enter both a wavelength variable terahertz wave source using a nonlinear optical crystal and a terahertz wave detector using a nonlinear optical crystal.

In the embodiment, a light source capable of generating near-infrared light is used as an excitation light source. In the following description, near-infrared light generated from the excitation light source will be simply called "excitation light".

In the generation and the detection of the terahertz wave, the excitation light needs to satisfy angle phase matching conditions inside each nonlinear optical crystal. The angle phase matching conditions are angle conditions between a light wave necessary for wavelength conversion and the terahertz wave. In the conditions, an energy conservation law ($\omega_P = \omega_S + \omega_T$; $\omega_P$ denoting excitation light, $\omega_S$ denoting Stokes ray, and $\omega_T$ denoting terahertz wave) and a momentum conservation law ($k_P = k_S + k_T$; $k_P$ denoting excitation light, $k_S$ denoting Stokes ray, and $k_T$ denoting terahertz wave) are satisfied. In the description below, the Stokes ray will be called an "idler beam".

If an incidence angle θ of the excitation light to each nonlinear optical element is changed to satisfy the angle phase matching conditions, the wavelength of the terahertz wave used in the terahertz wave generation/detection system can be changed. The terahertz wave generation/detection system described below provides a mechanism that can change the terahertz wave across a wide band through variable control of the incidence angles θ and that can accurately and quickly detect the terahertz wave at room temperature at the same time.

(B) Summary of System

Figure 1:
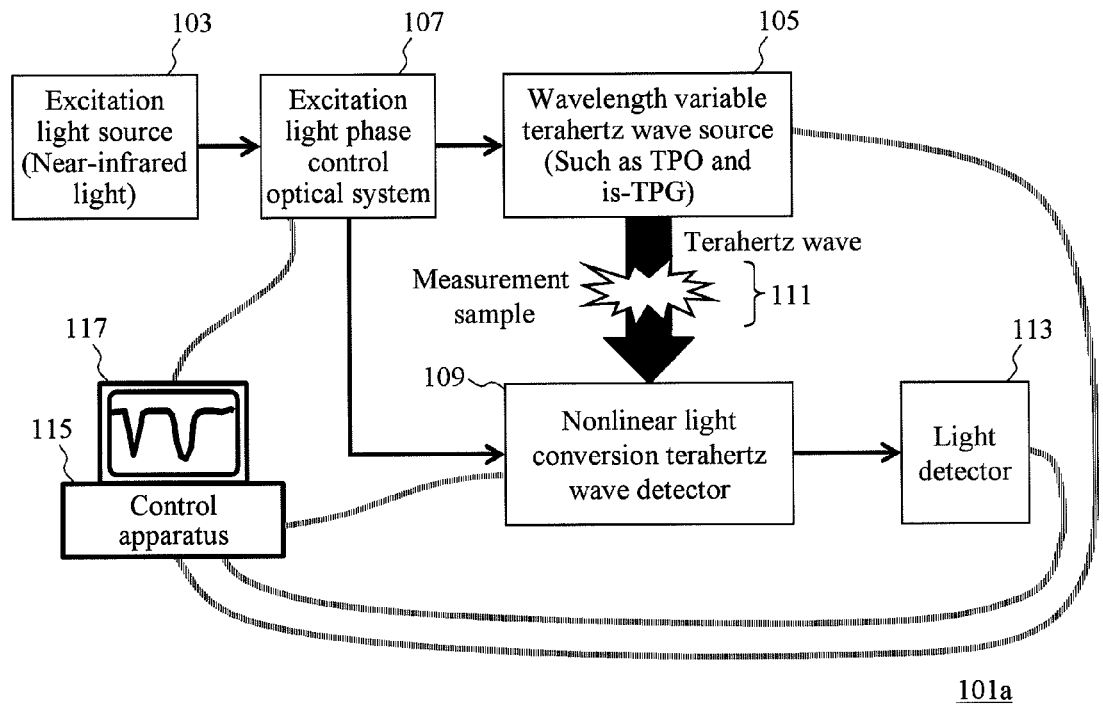
FIGS. 1A and 1B are diagrams showing a conceptual configuration example of a terahertz wave generation/detection system.
Figure 1:
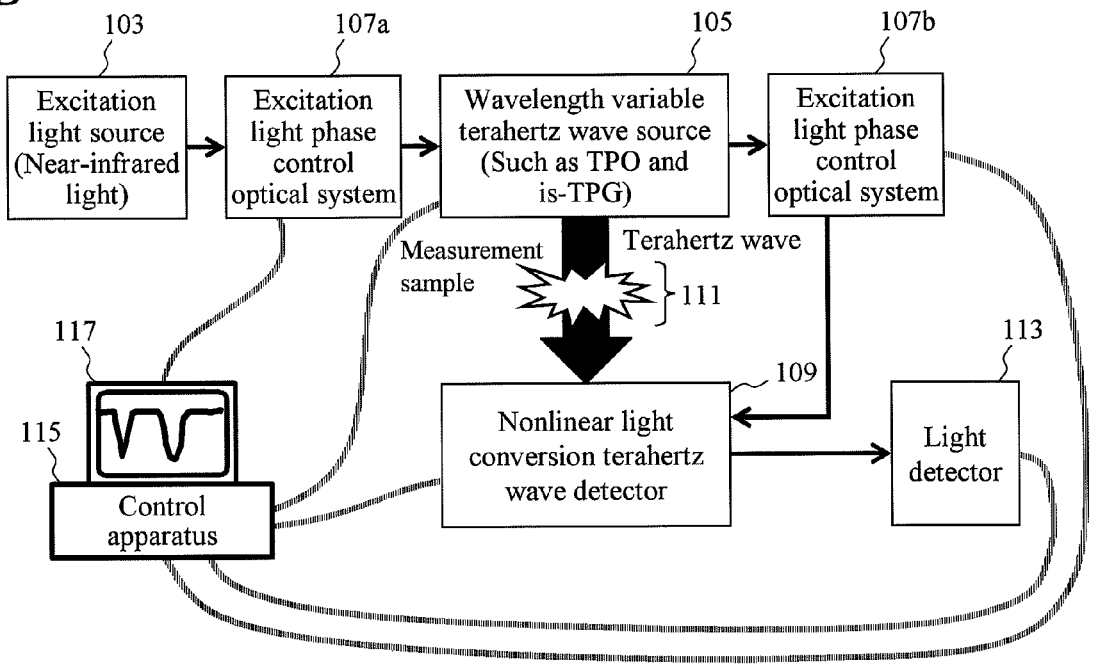

FIGS. 1A and 1B show conceptual configurations of a monochromatic wavelength variable terahertz wave generation/detection system. As shown in FIGS. 1A and 1B, the terahertz wave generation/detection system can have two types of configurations, a system shown in FIG. 1A and a system shown in FIG. 1B.

A terahertz wave generation/detection system 101a shown in FIG. 1A adopts a system of dividing one excitation light into two, causing one of the excitation light to enter a wavelength variable terahertz wave source 105, and causing the other excitation light to enter a nonlinear light conversion terahertz wave detector 109. In the system, the excitation light is divided into two before entering the wavelength variable terahertz wave source 105.

The terahertz wave generation/detection system 101a adopting the system comprises one excitation light source 103, the wavelength variable terahertz wave source 105, an excitation light phase control optical system 107, the nonlinear light conversion terahertz wave detector 109, a terahertz wave phase control optical system 111, a light detector 113, a control apparatus 115, and a display apparatus 117.

The excitation light source 103 is a light source in which near-infrared light is generated as excitation light. As shown in FIG. 1A, there is one excitation light source 103. Since there is one excitation light source 103, high coherence is expected between the terahertz wave and the excitation light in the detection. As a result, the detection sensitivity of the terahertz wave can be improved.

The wavelength variable terahertz wave source 105 is a light source that generates a terahertz wave by causing the excitation light to enter a nonlinear optical crystal to satisfy the angle phase matching conditions. The wavelength variable terahertz wave source 105 includes several light sources with different generation methods of terahertz wave. For example, a THz-wave parametric oscillator (TPO) using an oscillator or a THz-wave parametric generator (TPG) not including an oscillator is used.

The excitation light phase control optical system 107 is an optical system that divides the excitation light into two and that leads the lights to the wavelength variable terahertz wave source 105 and the nonlinear light conversion terahertz wave detector 109 to satisfy the angle phase matching conditions. The excitation light phase control optical system 107 comprises an optical element arranged to set both a generation point of the terahertz wave in the wavelength variable terahertz wave source 105 and an incidence point of the terahertz wave in the nonlinear light conversion terahertz wave detector 109 on the focal points in the confocal optical system.

The optical element that adjusts the wavelength of the generated terahertz wave (i.e. optical element that adjusts the incidence angle to the nonlinear optical crystal) is arranged on a light path before the division of the excitation light. The arrangement allows a synchronous change in the incidence angles θ of the excitation light on the generation side and the detection side of the terahertz wave. The incidence angles θ may be continuously changed or noncontinuously (step by step) changed.

The nonlinear light conversion terahertz wave detector 109 is an optical device that causes the terahertz wave and the excitation light after passing through a measurement sample to enter the nonlinear optical crystal and that converts the wavelength of a terahertz wave to form a light wave. Obviously, the terahertz wave and the excitation light satisfy the angle phase matching conditions.

The terahertz wave phase control optical system 111 is an optical system comprising: an optical system that leads the terahertz wave generated by the wavelength variable terahertz wave source 105 to the measurement sample; and an optical system that leads the terahertz wave transmitted through the measurement sample to the nonlinear light conversion terahertz wave detector 109 to satisfy the angle phase matching conditions.

The light detector 113 is a device that detects a light wave generated through the wavelength conversion in the nonlinear light conversion terahertz wave detector 109. For example, the light detector 113 comprises a photoelectric conversion element. The light intensity detected by the light detector 113 is provided to the control apparatus 115 as an electrical signal.

The control apparatus 115 is a control unit that controls at least one of the wavelength variable terahertz wave source 105, the excitation light phase control optical system 107, the nonlinear light conversion terahertz wave detector 109, the terahertz wave phase control optical system 111, and the light detector 113. The control apparatus 115 comprises, for example, a computer. The control apparatus 115 also executes signal processing for generating a graph showing the relationship between the wavelength of the terahertz wave and the detected light intensity.

The display apparatus 117 is one of the peripheral apparatuses of the control apparatus 115 and is used to, for example, display a measurement result.

Other than the display apparatus 117, an output apparatus such as a printer, input apparatuses such as a keyboard and a mouse, and a network terminal are connected to the control apparatus 115, and interfaces for connection to the devices are mounted in the control apparatus 115.

Meanwhile, the terahertz wave generation/detection system 101b shown in FIG. 1B adopts a system of also using the excitation light, which is used in the generation of the terahertz wave in the wavelength variable terahertz wave source 105, to detect the terahertz wave in the nonlinear light conversion terahertz 109.

The terahertz wave generation/detection system 101b adopting the system comprises one excitation light source 103, the wavelength variable terahertz wave source 105, two excitation light phase control optical systems 107a and 107b, the nonlinear light conversion terahertz wave detector 109, the terahertz wave phase control optical system 111, the light detector 113, the control apparatus 115, and the display apparatus 117.

Configurations specific to the terahertz wave generation/detection system 101b are the two excitation light phase control optical systems 107a and 107b, and other parts are basically the same as those in the terahertz wave generation/detection system 101a. Obviously, the excitation light phase control optical systems 107a and 107b also function to lead the excitation light to satisfy the angle phase matching conditions in the wavelength variable terahertz wave source 105 and the nonlinear light conversion terahertz wave detector 109. The differences include: the excitation light phase control optical system 107a is an optical system that leads the excitation light to the wavelength variable terahertz wave source 105 to satisfy the angle phase matching conditions; and the excitation light phase control optical system 107b is an optical system that leads the excitation light to the nonlinear light conversion terahertz wave detector 109 to satisfy the angle phase matching conditions.

In the excitation light phase control optical systems 107a and 107b, the optical elements are also arranged to set both the generation point of the terahertz wave in the wavelength variable terahertz wave source 105 and the incidence point of the terahertz wave in the nonlinear light conversion terahertz wave detector 109 on the focal points in the confocal optical system.

In the terahertz wave generation/detection system 101b, the optical element that adjusts the wavelength of the generated terahertz wave (i.e. optical element that adjusts the incidence angle to the nonlinear optical crystal) is arranged only in the excitation light phase control optical system 107a. The arrangement allows a synchronous change in the incidence angles θ of the excitation light on the generation side and the detection side of the terahertz wave. Similarly, the incidence angles θ may be continuously changed or noncontinuously (step by step) changed.

(C) Experimental Apparatus Example (C-1) Experimental Apparatus Example 1

Figure 2:
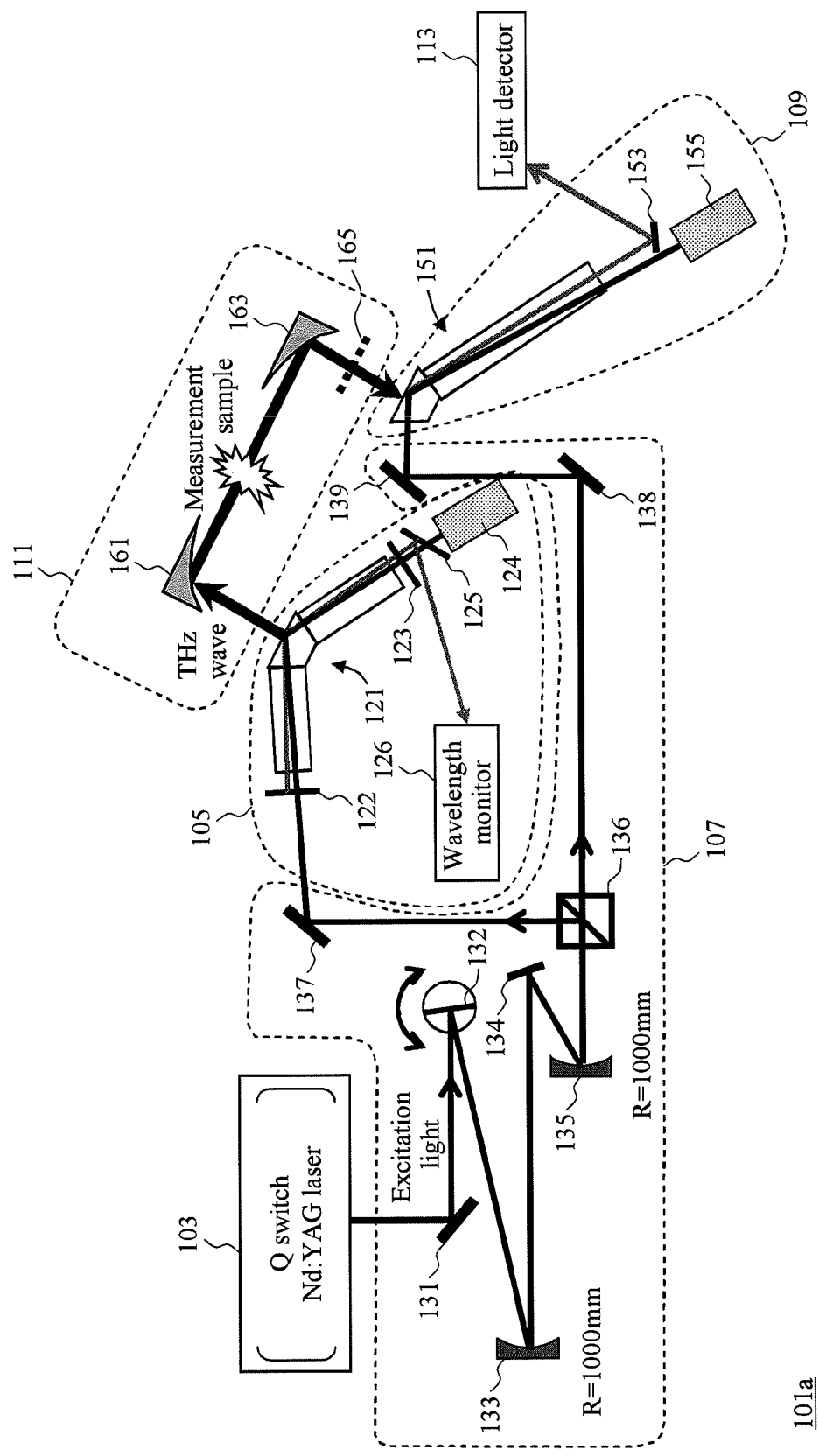
FIG. 2 is a diagram showing an experimental apparatus example of the terahertz wave generation/detection system.

FIG. 2 shows an experimental apparatus example corresponding to the terahertz wave generation/detection system 101a (FIG. 1A). In FIG. 2, the parts corresponding to FIG. 1A are designated with the same reference numerals.

(Excitation Light Source)

In the case of the experimental apparatus, a near-infrared pulse laser source is used for the excitation light source 103. Examples of the near-infrared pulse laser source include a Q switch Nd:YAG laser, a Q switch Nd:YVO$_4$ laser, and a Yb fiber laser.

(Wavelength Variable Terahertz Wave Source)

Figure 3:
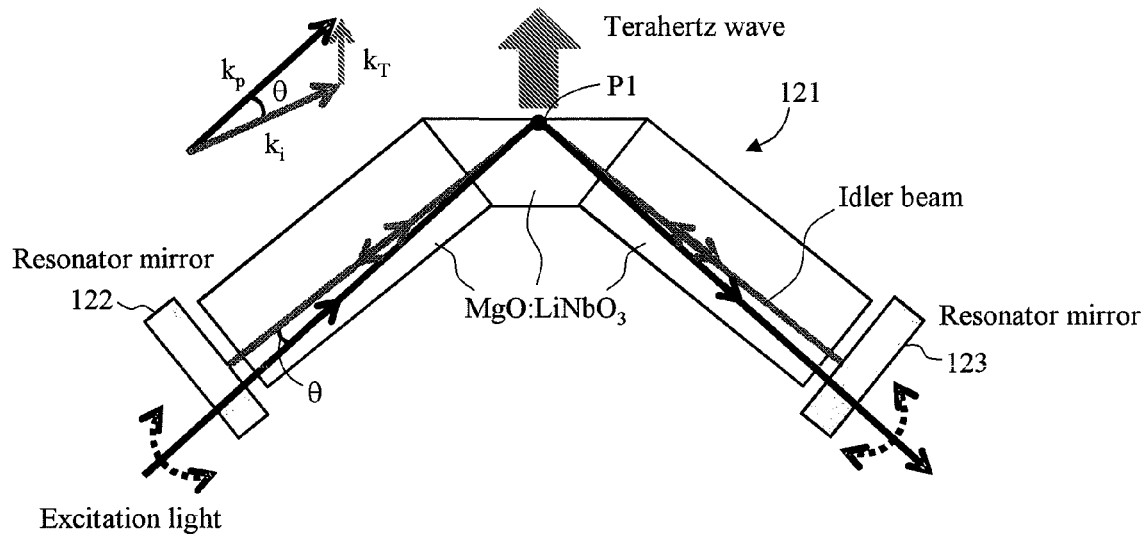
FIG. 3 is a diagram showing an example of configuration of a surface-output terahertz wave parametric oscillator.

FIG. 3 shows an experimental apparatus example of the wavelength variable terahertz wave source 105. FIG. 3 illustrates a case in which the wavelength variable terahertz wave source 105 is a surface-output terahertz wave parametric oscillator (hereinafter, called "surface-output TPO").

In the surface-output TPO shown in FIG. 3, a nonlinear optical crystal 121 including rectangular solid shaped crystals attached to two oblique surfaces of a crystal processed into a trapezoid pillar shape is used. For example, 5% magnesium-doped lithium niobate (MgO:LiNbO3) is used for the nonlinear optical crystal 121. In the nonlinear optical crystal 121, the excitation light and the idler beam (Stokes ray) are totally reflected at one point (called a generation point P1 in the specification) on the crystal surface which is a bottom face of the trapezoid pillar, and meanwhile, the terahertz wave is emitted outside the crystal.

The direction of the emission of the terahertz wave is provided by a vector diagram shown in FIG. 3. The angular relationship satisfies the angle phase matching conditions when the total reflection of the excitation light, etc. and the external output of the terahertz wave occur at the generation point P1 as shown in FIG. 3.

Resonator mirrors 122 and 123 are arranged outside both end surfaces of the nonlinear optical crystal 121. The resonator mirrors 122 and 123 are used to confine the idler beam in the resonators for oscillation. The resonator mirror 122 transmissively receives the excitation light, and the resonator mirror 123 transmissively emits the excitation light. The incidence angle of the excitation light to the nonlinear optical crystal 121 is provided as an angle θ formed by the excitation light and the idler beam.

A beam damper 124 that terminates the excitation light transmitted through the resonator mirror 123 and an observation optical system (a half mirror 125 and a wavelength monitor 126) of the idler light are arranged on the wavelength variable terahertz wave source 105. The half mirror 125 is an optical element that reflects the idler beam outputted from the resonator mirror 123 for detecting the wavelength of the generated terahertz wave toward a light receiving surface of the wavelength monitor 126 while passing the excitation light. In this way, the resonator mirror 123 is configured to be able to basically confine the idler beam in the resonator but to extract part of the idler beam for monitoring the terahertz wave.

(Excitation Light Phase Control Optical System)

The excitation light phase control optical system 107 is an optical system that realizes the variable control of the angle phase matching conditions outside the wavelength variable terahertz wave source 105. More specifically, the excitation light phase control optical system 107 operates to alter the optical axis of the excitation light to change the incidence angle θ of the excitation light to the nonlinear optical crystal 121 to alter the phase matching angle at the generation point P1. To obtain optimal wavelength conversion even if the phase matching angle is changed, the system needs to be optically designed so that the excitation light surely passes through the generation point P1 of the nonlinear optical crystal 121. The condition related to the phase matching angle also needs to be satisfied in the nonlinear light conversion terahertz wave detector 109. Therefore, an optical system capable of simultaneously realizing the control of the incidence angles θ in both the generation and the detection of the terahertz wave is needed. Consequently, the present inventors propose a method of using a confocal optical system to control the phase matching angles to obtain optimal phase matching angles in both the generation and the detection at the same time.

Figure 4:
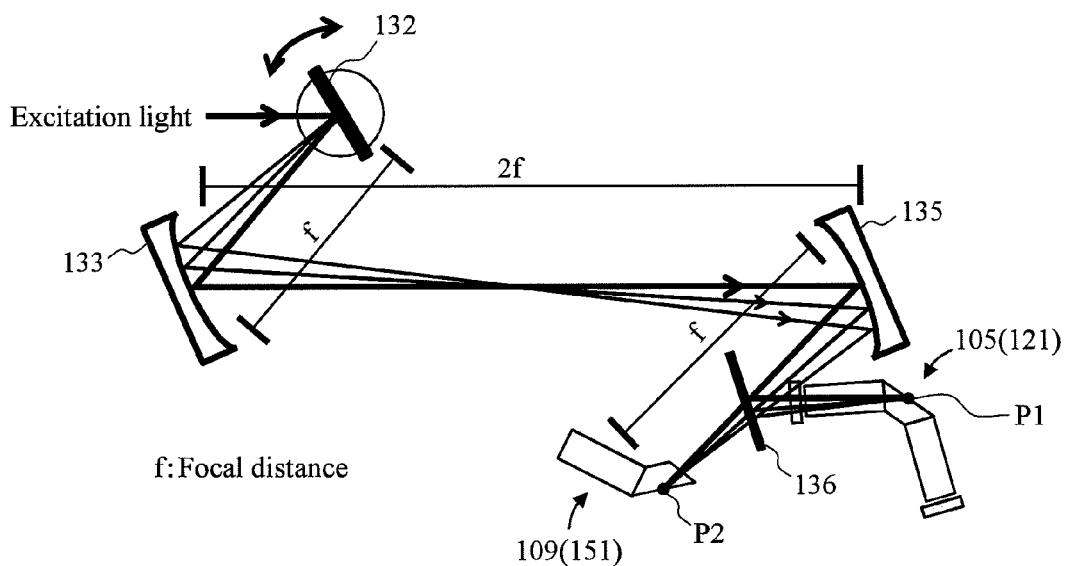
FIG. 4 is a diagram showing a confocal optical system.

FIG. 4 shows an example of the confocal optical system. The confocal optical system used in the experimental apparatus comprises a plurality of lenses (concave mirrors 133 and 135), mirrors (131, 132, 134, 137, 138, and 139), and a beam splitter 136. In the confocal optical system, focal positions of the entire optical system are arranged on a surface of the mirror 132 arranged on a galvano scanner, on a total reflection surface of the nonlinear optical crystal 121 in the surface-output TPO (generation point P1), and on a total reflection surface of a nonlinear optical crystal 151 in the nonlinear light conversion terahertz wave detector 109 (incidence point P2).

In the confocal optical system, even if the mirror 132 arranged on the galvano scanner is rotated, the excitation light always passes through the other two focuses, and only the incidence angles θ of the excitation light to the nonlinear optical crystals 121 and 151 change. Thus, the same phase matching angle conditions can be realized on the generation side and the detection side at the same time. Therefore, optimal conditions can be realized on the generation side and the detection side at the same time. The terahertz wave can also be highly efficiently detected at the same time while changing the wavelength of the terahertz wave by altering the incidence angle θ. Moreover, the excitation light is light emitted from the single excitation light source 103, and high coherence between the generation side and the detection side of the terahertz wave can be maintained.

The mirror 132 is arranged on the galvano scanner. Therefore, the mirror 132 can be quickly scanned at room temperature. The control of the fast scan allows continuous or non-continuous (step by step) change in the wavelength of the generated terahertz wave. The galvano scanner used in the experiment has a capability of changing the wavelength millisecond by millisecond.

Figure 5:
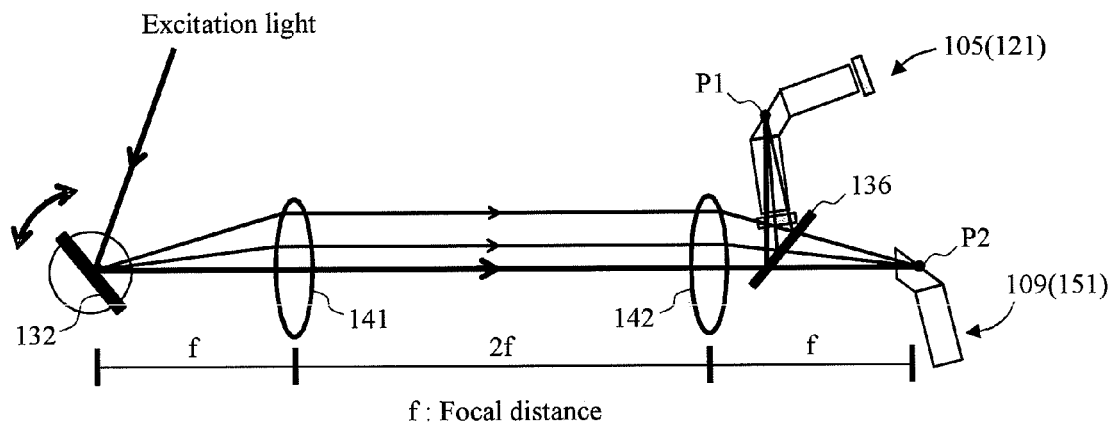
FIG. 5 is a diagram showing another confocal optical system.

The excitation light phase control optical system 107 can also be realized by a structure using convex lenses 141 and 142 as shown in FIG. 5.

As described, the confocal optical system can be realized using a plurality of lenses and mirrors. However, the image magnification of the confocal optical system needs to be handled carefully. In the experiment, a concave mirror with focal distance f500 mm is used to make the image magnification 1:1. If the confocal optical system is designed in consideration of the image magnification, similar beam steering control is possible while enlarging and reducing the beam size.

(Nonlinear Light Conversion Terahertz Wave Detector)

The experimental apparatus uses a nonlinear optical effect to convert the wavelength (up-conversion) of the terahertz wave to form a light wave to indirectly detect the terahertz wave through the light wave. The detection method is excellent for improving the detection accuracy of the terahertz wave, because technically progressed various light detectors 113 can be used.

Figure 6:
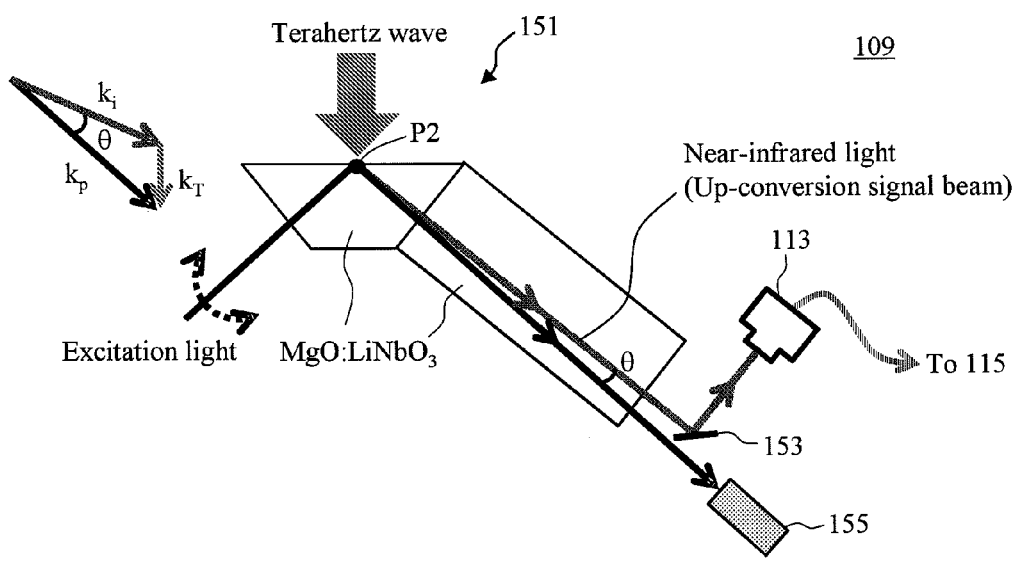
FIG. 6 is a diagram showing an example of configuration of a nonlinear light conversion terahertz wave detector.

FIG. 6 shows an experimental apparatus example of the nonlinear light conversion terahertz wave detector 109. The nonlinear light conversion terahertz wave detector 109 uses the nonlinear optical crystal 151 including a rectangular solid shape crystal attached to one of the oblique surfaces of a crystal processed into a trapezoid pillar shape. The nonlinear optical crystal 151 is also formed by, for example, 5% magnesium-doped lithium niobate ($MgO:LiNbO_3$).

In the experimental apparatus, the terahertz wave enters the nonlinear optical crystal 151, while a parabolic mirror 163 of the terahertz wave phase control optical system 111 narrows down the beam diameter. The terahertz wave enters substantially perpendicular to one point (called "incidence point P2" in the specification) on a crystal surface which is the bottom face of the trapezoid pillar. The excitation light enters the crystal processed into a trapezoid pillar shape from an oblique surface on a side that is not attached to the rectangular solid shape crystal. As described, the excitation light enters the crystal so that the incidence point P2 matches a focal point in the confocal optical system. Obviously the excitation light is properly controlled to satisfy the phase matching angle.

Therefore, when the terahertz wave and the excitation light are mixed at the incidence point P2, near-infrared light is generated. The relationship between the generation direction of the near-infrared light and the incidence direction of the terahertz wave is provided by a vector diagram shown in FIG. 6. In this way, the angular relationship when the excitation light and the terahertz wave are mixed is set to satisfy the angle phase matching conditions at the incidence point P2. The near-infrared light is outputted from the nonlinear optical crystal at an angle θ relative to the excitation light that is totally reflected at the incidence point P2. Obviously, the near-infrared light is not generated when there is no incidence of the terahertz wave.

The near-infrared light is separated from the excitation light in the nonlinear optical crystal 151 and is detected by the light detector 113. A mirror 153 that leads the near-infrared light to the light detector 113 is arranged in the experimental apparatus. A beam damper 155 is arranged to terminate the excitation light emitted from the nonlinear optical crystal 151.

The wavelength conversion from the terahertz wave to the near-infrared light in the nonlinear optical crystal 151 can be realized at room temperature.

(Terahertz Wave Phase Control Optical System)

The terahertz wave phase control optical system 111 is an optical system that leads the terahertz wave generated at the generation point P1 of the wavelength variable terahertz wave source 105 to the measurement sample and that leads the terahertz wave transmitted through or reflected by the measurement sample to the incidence point P2 of the nonlinear light conversion terahertz wave detector 109. In the experimental apparatus, the terahertz wave phase control optical system 111 is constituted by a pair of parabolic mirrors 161 and 163. In the experimental apparatus shown in FIG. 2, the measurement sample is arranged on the light path between the parabolic mirrors 161 and 163. An attenuator 165 that reduces the beam intensity is arranged as necessary on the light path between the parabolic mirror 163 and the incidence point P2 of the nonlinear light conversion terahertz wave detector 109. The measurement sample may be arranged on the light path between the parabolic mirror 163 and the incidence point P2 of the nonlinear light conversion terahertz wave detector 109.

(Light Detector)

In the experimental apparatus, an InGaAs light detector is used as the light detector 113. The nonlinear light conversion terahertz wave detector converts the terahertz wave, which is a nanosecond pulse, into near-infrared light, and the use of the InGaAs light detector allows measurement in the same time scale.

(Control Apparatus)

In the experimental apparatus, the control apparatus 115 electronically controls the rotation angle of the mirror 132 arranged on the galvano scanner to control the angle phase matching conditions of the excitation light, and the variable control of the wavelength of the terahertz wave is performed through the control. The control apparatus 115 executes a process of generating a graph showing the relationship between the detection result (light intensity) of the light detector 113 and the wavelength of the generated terahertz wave. The control apparatus 115 acquires information related to the wavelength of the terahertz wave based on wavelength information of the idler beam detected through the wavelength monitor 126.

(C-2) Experimental Apparatus Example 2

Figure 7:
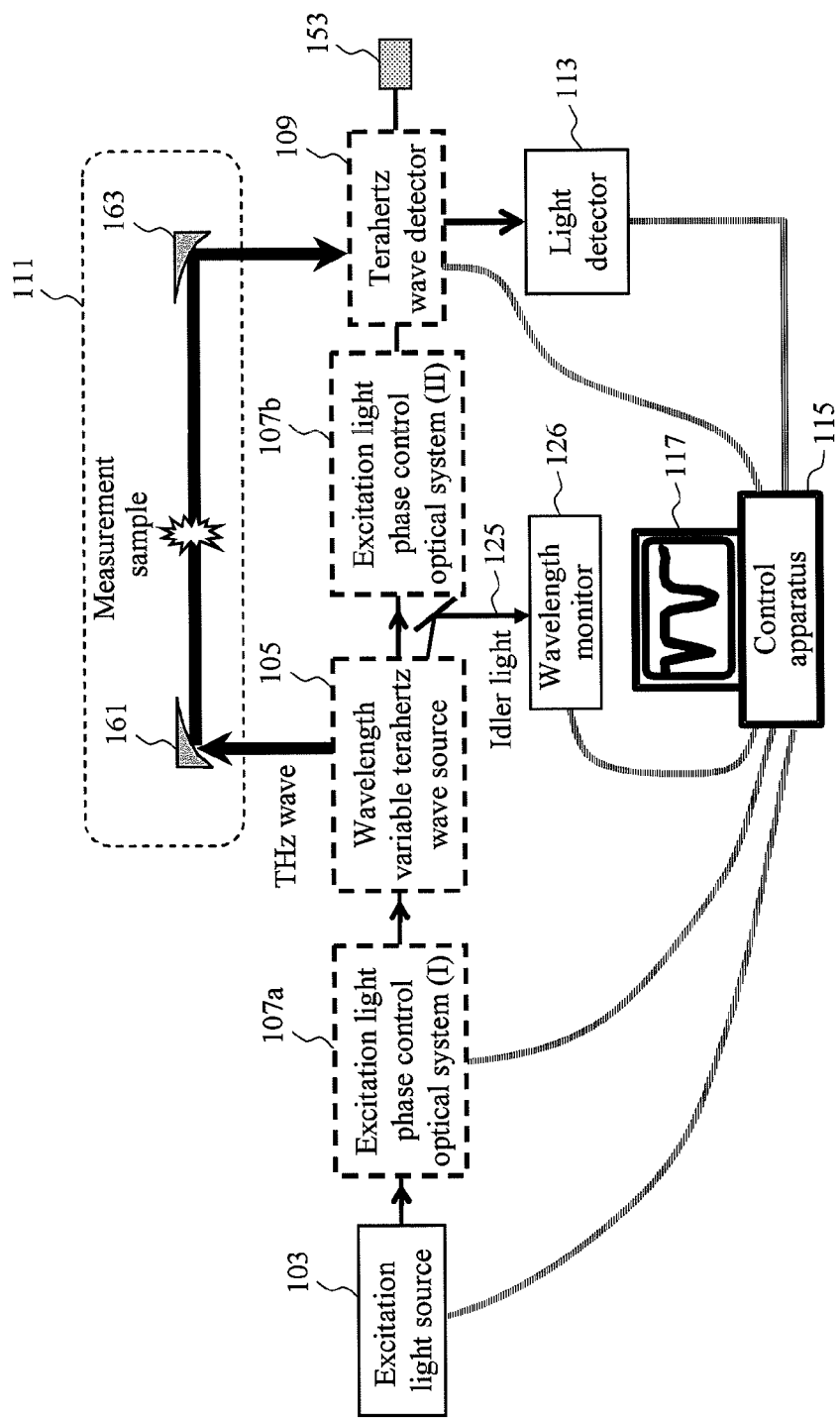
FIG. 7 is a diagram showing another experimental apparatus example of the terahertz wave generation/detection system.

FIG. 7 shows a conceptual configuration of an experimental apparatus corresponding to the terahertz wave generation/detection system 101b (FIG. 1B). The terahertz wave generation/detection system 101b is basically the same as the terahertz wave generation/detection system 101a except that two excitation light phase control optical systems 107 are prepared. Therefore, the parts corresponding to FIGS. 1B and 2 are designated with the same reference numerals in FIG. 7.

As shown in FIG. 7, one excitation light source 103, a first excitation light phase control optical system 107a, the wavelength variable terahertz wave source 105, a second excitation light phase control optical system 107b, and the nonlinear light conversion terahertz wave detector 109 are arranged in cascade in the terahertz wave generation/detection system 101b. More specifically, the excitation light enters the second excitation light phase control optical system 107b after transmitting through the first excitation light phase control optical system 107a and the wavelength variable terahertz wave source 105.

Hereinafter, the first excitation light phase control optical system 107a and the second excitation light phase control optical system 107b that are optical systems specific to the terahertz wave generation/detection system 101b will be described. The first excitation light phase control optical system 107a corresponds to a first confocal optical system of Claims, and the second excitation light phase control optical system 107b corresponds to a second confocal optical system in Claims.

Figure 8:
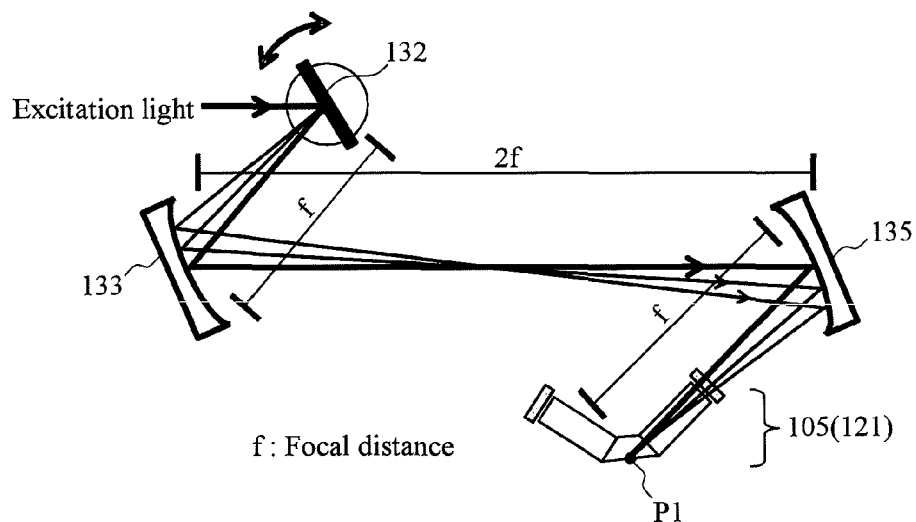
FIGS. 8A and 8B are diagrams showing a first confocal optical system.
Figure 8:
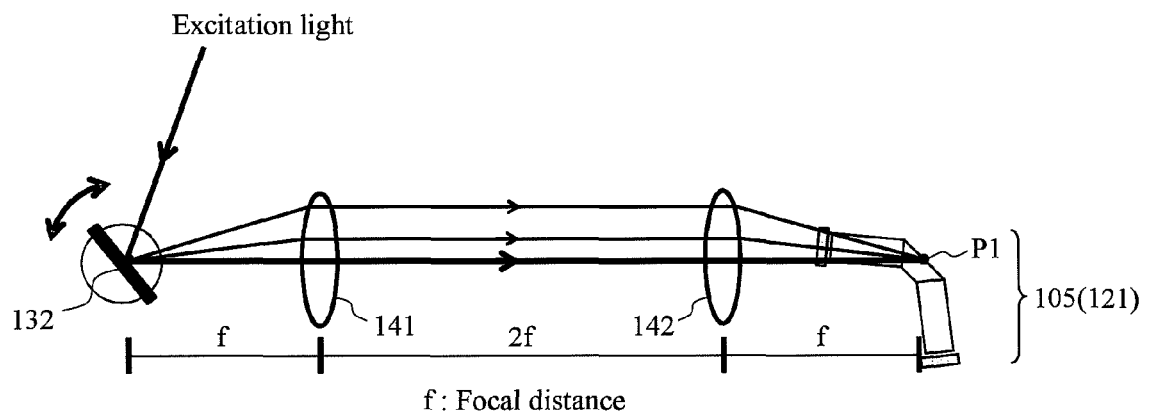

FIGS. 8A and 8B show experimental apparatus examples of the first excitation light phase control optical system 107a. FIG. 8A illustrates an example of configuring the confocal optical system using the concave mirrors 133 and 135, and FIG. 8B illustrates an example of configuring the confocal optical system using the lenses 141 and 142. In both cases, the focal positions of the confocal optical system are arranged on the surface of the mirror 132 arranged on the galvano scanner and on the total reflection surface (generation point P1) of the nonlinear optical crystal 121 in the surface-output TPO. According to the configuration, even if the mirror 132 arranged on the galvano scanner is rotated, the excitation light always enters the generation point P1 of the nonlinear optical crystal 121, and only the incidence angle θ to the generation point P1 changes.

Figure 9:
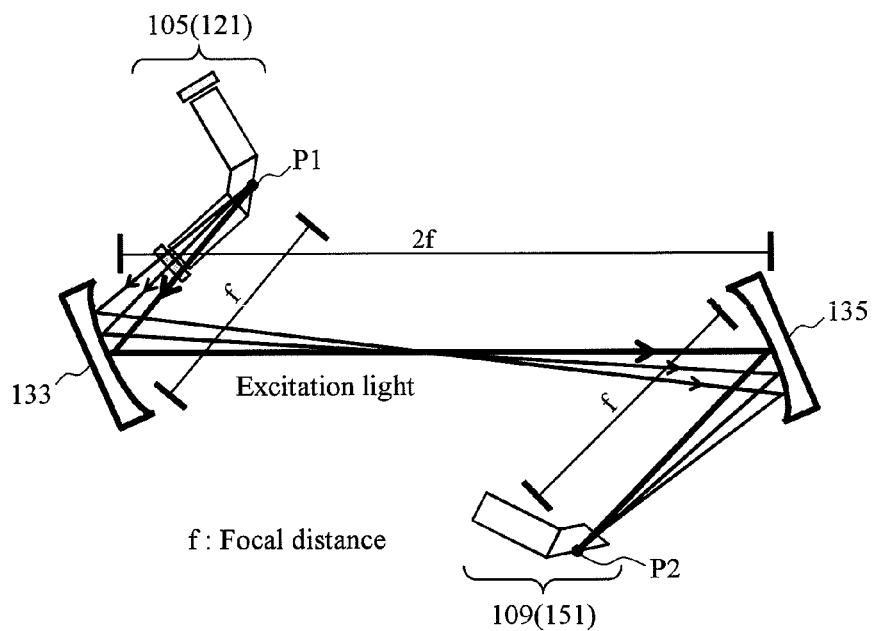
FIGS. 9A and 9B are diagrams showing a second confocal optical system.
Figure 9:
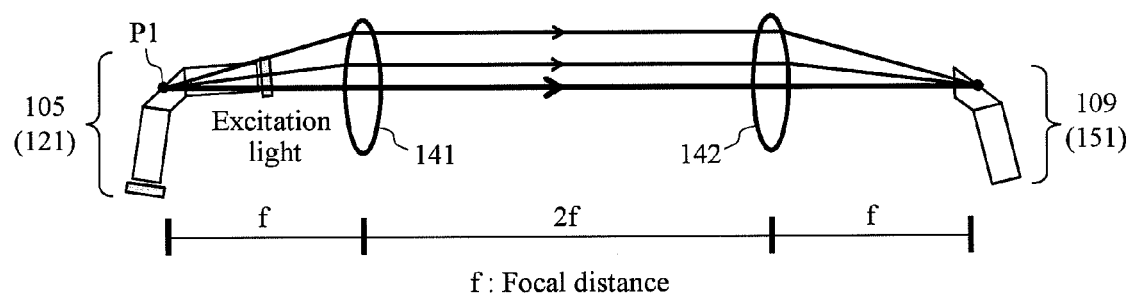

FIGS. 9A and 9B show experimental apparatus examples of the second excitation light phase control optical system 107b. FIG. 9A shows an example of configuring the confocal optical system using the concave mirrors 133 and 135, and FIG. 9B shows an example of configuring the confocal optical system using the lenses 141 and 142. In both cases, the focal positions of the confocal optical system are arranged on the total reflection surface (generation point P1) of the nonlinear optical crystal 121 in the surface-output TPO and on the total reflection surface (incidence point P2) of the nonlinear optical crystal 151 in the terahertz wave detector 109. Therefore, even if the rotation of the mirror 132 arranged on the galvano scanner changes the emission angle (same as the incidence angle θ) of the excitation light totally reflected at the generation point P1, the excitation light always enter the incidence point P2 of the nonlinear optical crystal 151, and only the incidence angle θ to the incidence point P2 changes.

In this way, when the system of propagating the excitation light in cascade is implemented, the phase matching angles on the generation side and the detection side can be controlled at the same time by only controlling the rotation of the mirror 132 arranged on the galvano scanner. Therefore, the optimal conditions can be realized at the same time on both the generation side and the detection side. Furthermore, the terahertz wave can be highly efficiently detected at the same time while changing the wavelength of the terahertz wave by altering the incidence angle θ. Moreover, the excitation light is light emitted from the single excitation light source 103, and high coherence between the generation side and the detection side of the terahertz wave can be maintained.

The terahertz wave phase control optical system 111, the light detector 113, the control apparatus 115, and the display apparatus 117 are also arranged in the terahertz wave generation/detection system 101b. The control apparatus 115 acquires information related to the wavelength of the terahertz wave based on wavelength information of the idler beam detected through the wavelength monitor 126.

(C-3) Other Experimental Apparatus Examples

Other examples of structure of the wavelength variable terahertz wave source and the nonlinear light conversion terahertz wave detector suitable for application to the experimental apparatus will be described.

(1) Wavelength Variable Terahertz Wave Source

Figure 10:
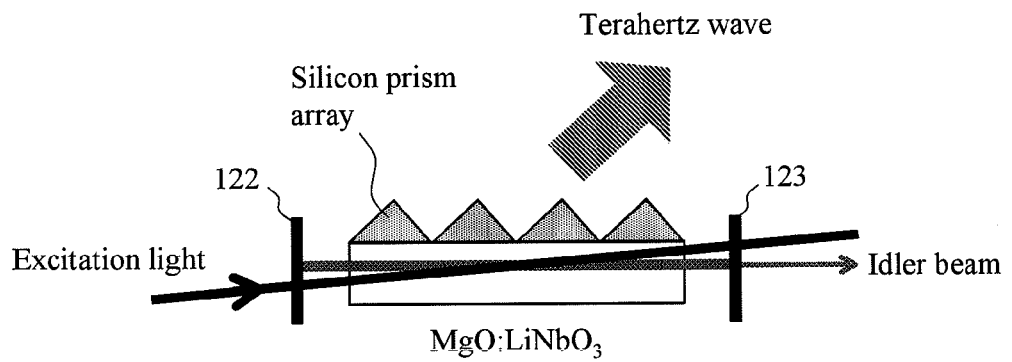
FIG. 10 is a diagram showing another example of structure of a wavelength variable terahertz wave source.

FIG. 10 shows an example of structure of a terahertz wave parametric oscillator (TPO). FIG. 10 conceptually shows an operational principle of a light source utilizing a nonlinear optical effect used. FIG. 10 shows an example of structure of an oscillator including a silicon prism array attached to a side of a lithium niobate crystal (MgO:LiNbO$_3$) as a nonlinear optical crystal. In the silicon prism array, a plurality of prisms including triangular cross sections are arranged in the travelling direction of the excitation light. Therefore, in FIG. 10, the cross sections of the prisms are parallel to the surface of the paper, and the height direction is perpendicular to the surface of the paper. In the oscillator configured this way, the incidence of excitation light generates an idler beam and a terahertz wave. Of these, the idler beam oscillates as two resonator mirrors 122 and 123 arranged at both ends of the nonlinear optical crystal confine the idler beam. Part of the idler beam confined by the resonator mirrors 122 and 123 is outputted outside from the resonator mirror 123 for monitoring of the oscillation state in the resonators or the wavelength of the generated terahertz wave. The terahertz wave is emitted into the space from a side of the lithium niobate crystal through the silicon prism array. The silicon prism array is attached to highly efficiently extract the terahertz wave to the outside by preventing the total reflection of the terahertz wave. In the structure, an intersection point of the excitation light and the idler beam corresponds to the generation point P1 of the terahertz wave.

Figure 11:
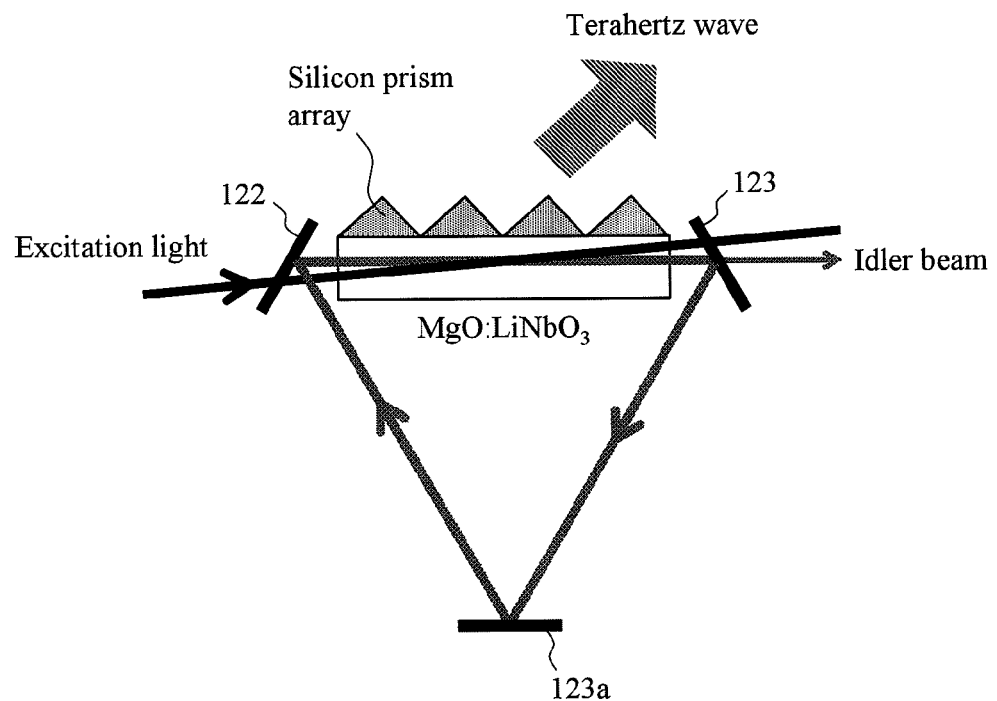
FIG. 11 is a diagram showing another example of structure of the wavelength variable terahertz wave source.

FIG. 11 illustrates an example of structure of a ring terahertz wave parametric oscillator. The basic principle for generating the terahertz wave is the same as the resonator shown in FIG. 10. However, in the resonator shown in FIG. 11, the idler beam rotates and oscillates in one direction in the resonator. Since the idler beam rotates in the same direction as the travelling direction of the excitation light, the wavelength can be converted highly efficiently. A resonator mirror 123a is added to the resonator shown in FIG. 10 to rotate the idler beam in a ring shape in the resonator shown in FIG. 11.

Figure 12:
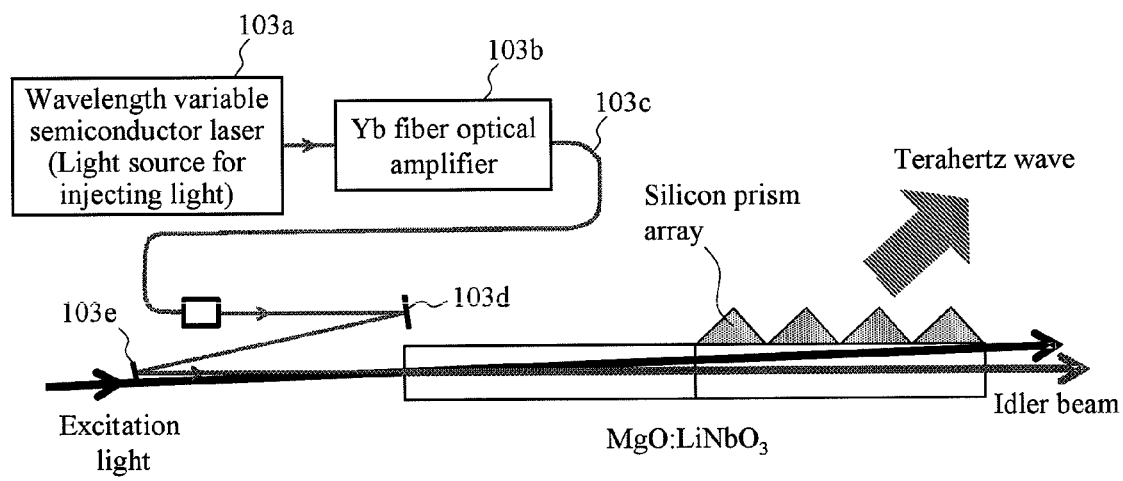
FIG. 12 is a diagram showing another example of structure of the wavelength variable terahertz wave source.

FIG. 12 shows an example of structure of a light-injection terahertz wave parametric generator. The wavelength variable terahertz wave source 105 shown in FIG. 12 does not include a resonator structure, and weak light as seed light is injected to the crystal from the outside. Therefore, in the generator shown in FIG. 12, a wavelength variable semiconductor laser 103a, a Yb fiber optical amplifier 103b, an optical fiber 103c, and reflection mirrors 103d and 103e are arranged on the front stage of the optical system including the silicon prism array attached to one surface of the lithium niobate crystal as the nonlinear optical crystal. The wavelength of the seed light is the same as the wavelength of the idler beam to be generated. In this way, in the light source shown in FIG. 12, the light wavelength of the wavelength variable semiconductor laser 103a is electronically controlled to adjust the wavelength of the terahertz wave. Therefore, the control apparatus 115 controls the incidence angle of the excitation light and controls the wavelength of the semiconductor laser at the same time in the terahertz wave generation/detection system using this type of light source.

(2) Nonlinear Light Conversion Terahertz Wave Detector

Figure 13:
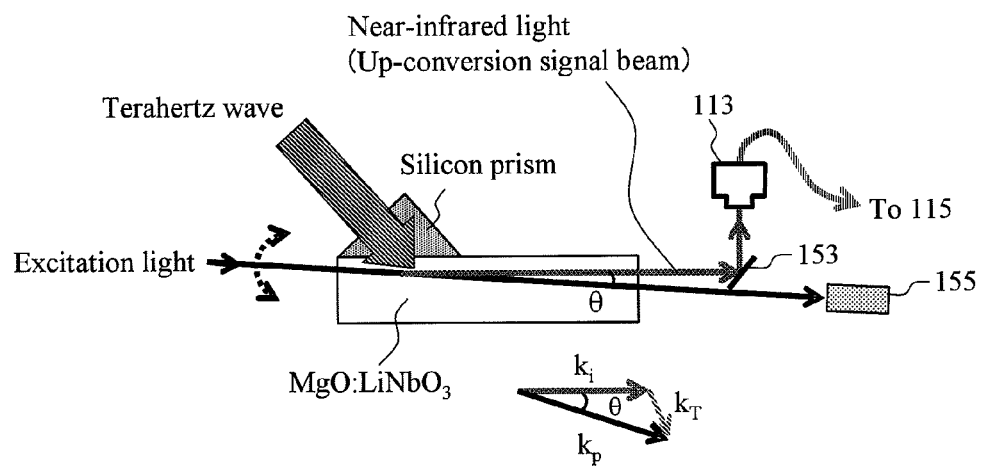
FIG. 13 is a diagram showing another example of structure of the nonlinear light conversion terahertz wave detector.

FIG. 13 shows another example of structure suitable for use in a nonlinear light conversion terahertz wave detector. The detector shown in FIG. 13 has a structure including one or more silicon prisms attached to one side of a lithium niobate crystal (MgO:LiNbO$_3$) as a nonlinear optical crystal. The nonlinear optical crystal has a rectangular solid shape. In FIG. 13, the cross sections of the silicon prisms are parallel to the surface of the paper, and the height direction is perpendicular to the surface of the paper. In the detector configured this way, the terahertz wave is led from the silicon prisms to a side of the nonlinear optical crystal. Meanwhile, the excitation light enters from one end surface of the nonlinear optical crystal.

The terahertz wave and the excitation light are mixed to satisfy the phase matching angle at the incidence point P2 set in the crystal. Therefore, near-infrared light can be generated at the incidence point P2 by the interaction between the terahertz wave and the excitation light when the terahertz wave enters. In this structure, the incidence point P2 is provided as an intersection of the excitation light and the terahertz wave.

(D) Result of Experiment

Figure 14:
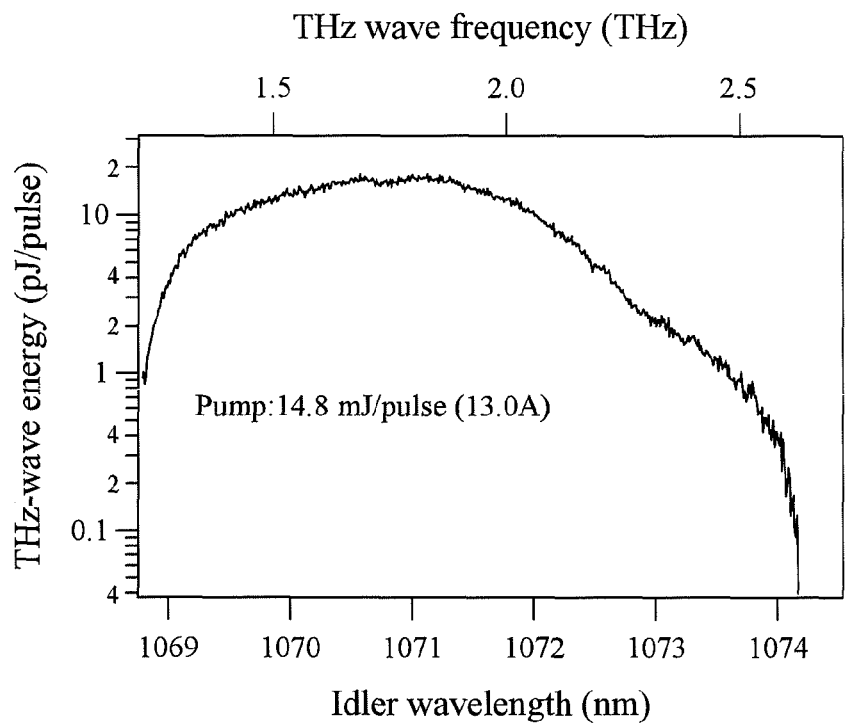
FIG. 14 is a diagram showing frequency-dependent characteristics of detected intensity.

A result of experiment obtained by the experimental apparatus will be illustrated. FIG. 14 shows a relationship of measurement between the frequency of the terahertz wave generated by the surface-output TPO (wavelength of idler beam) and the intensity of the terahertz wave. As shown in FIG. 14, the wavelength of the terahertz wave can be changed in a range of about 1.3 THz to 2.6 THz in the experiment. A commercially available cryogenic 4K silicon bolometer is used to detect the terahertz wave.

Figure 15:
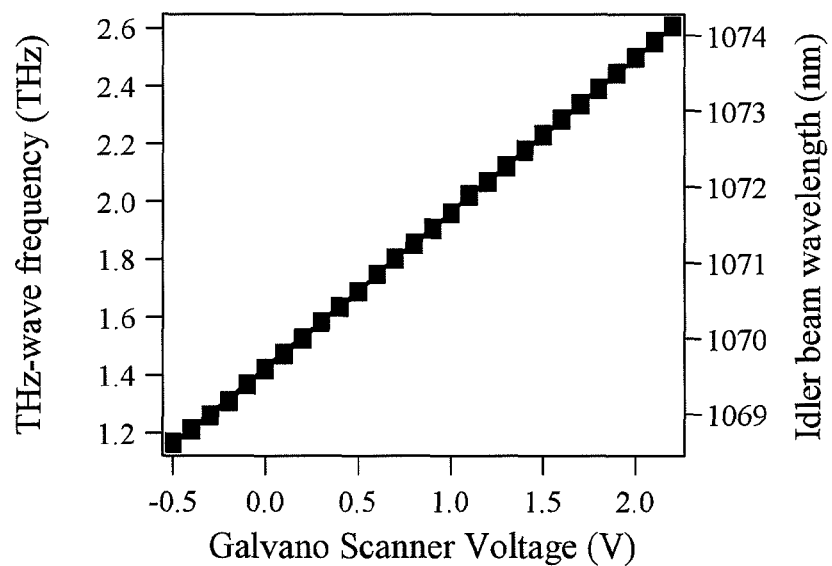
FIG. 15 is a diagram showing a relationship between applied voltage to a galvano scanner and generated terahertz frequency.

FIG. 15 shows a relationship between the galvano scanner applied voltage obtained by monitoring the wavelength of the idler beam and the terahertz wave frequency. As described, the galvano scanner can control the angle of the mirror 132 by applied voltage. The result of experiment shown in FIG. 15 can be similarly applied to the detection of the terahertz wave, and the result denotes center frequencies of the terahertz wave that can be detected by each voltage.

Figure 16:
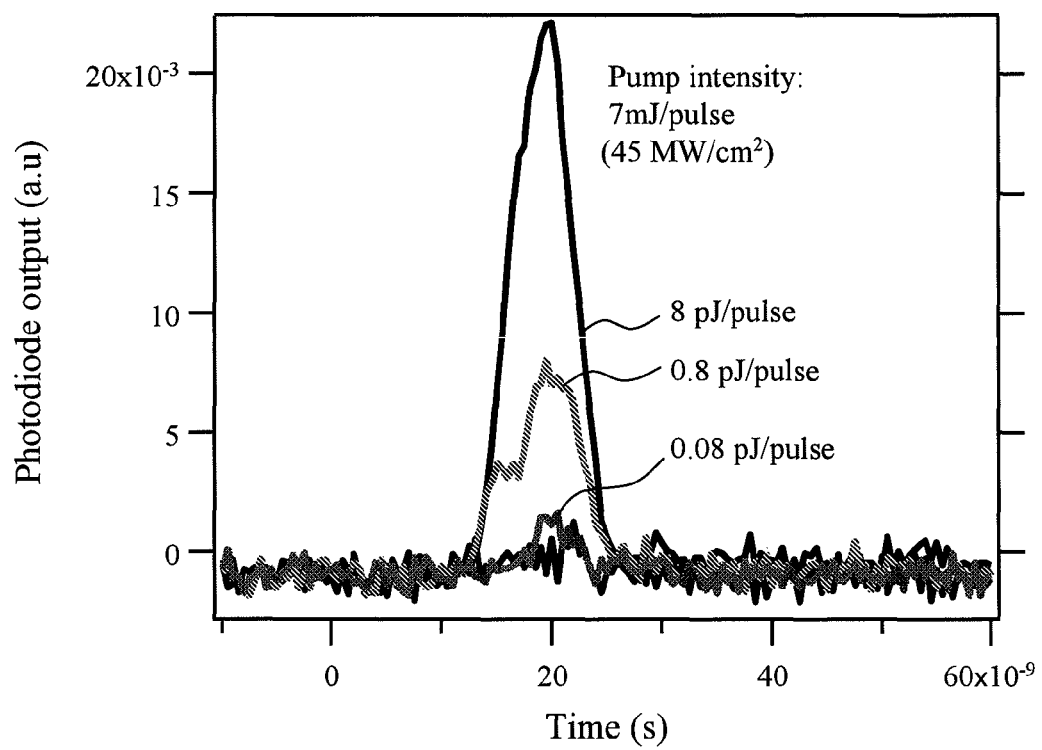
FIG. 16 is a diagram for explaining time resolving power of a detected terahertz wave.

FIG. 16 shows a result of measurement, by the experimental apparatus, of the terahertz wave generated by the surface-output TPO. The horizontal axis of FIG. 16 denotes time, indicating nanosecond order. Meanwhile, the vertical axis of FIG. 16 denotes output values of the InGaAs light detector. For example, if the terahertz wave output is changed from 8 pJ/pulse to 0.08 pJ/pulse, the output of the InGaAs light detector also decreases accordingly, and a double-digit dynamic range of terahertz wave detection can be obtained. At the same time, pulses up to a picosecond level can be captured as a time waveform.

When the attenuator 165 reduces the input energy of the terahertz wave to the light detector 113, a terahertz wave of about 0.1 pJ/pulse is measured in the experiment as minimum sensitivity.

Figure 17:
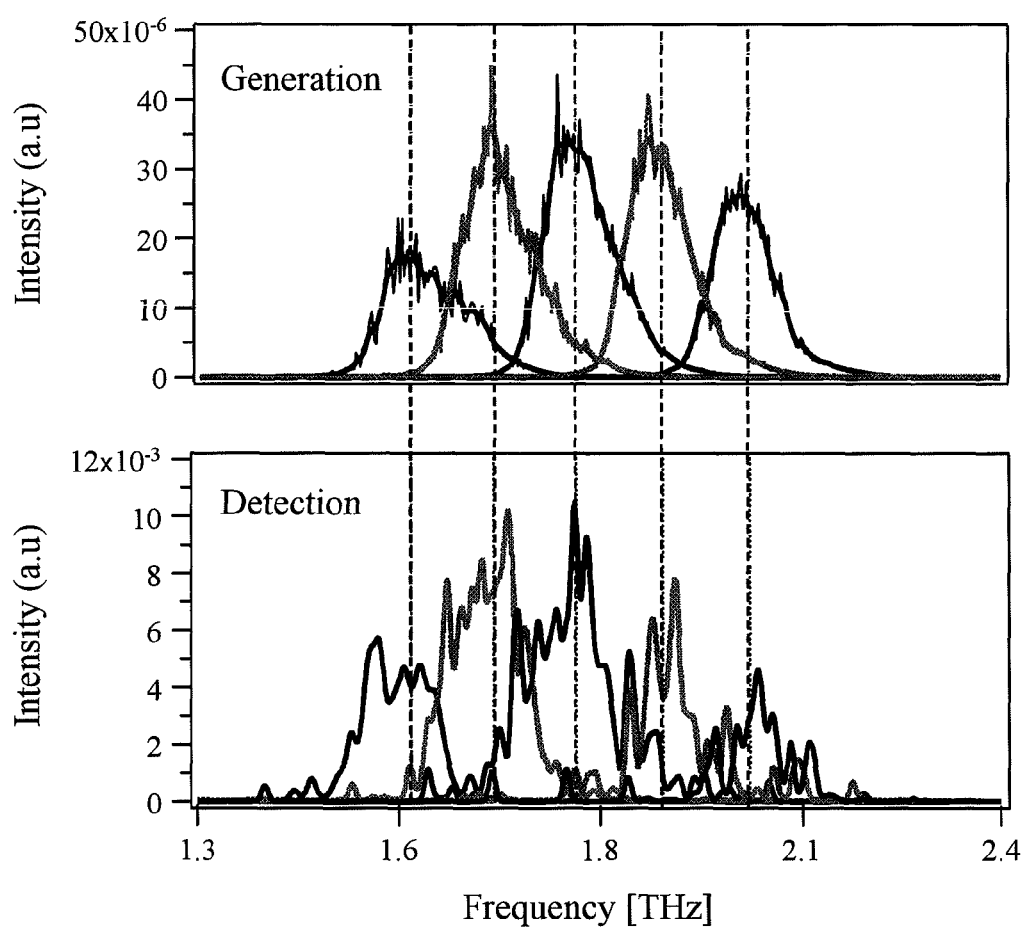
FIG. 17 is a diagram showing an example of monitor output when the frequency of the terahertz wave is changed.

FIG. 17 is a diagram showing a result of monitoring on the generation side and the detection side of the terahertz wave when the frequency of the terahertz wave is changed. The graph on the generation side denotes a result obtained by a spectrum analyzer detecting the idler beam generated at the same time with the terahertz wave. Meanwhile, the graph on the detection side denotes a result of the spectrum analyzer monitoring the near-infrared light obtained by the wavelength conversion. The horizontal axis of each graph denotes the frequency of the terahertz wave obtained from the wavelength of the detected light. The vertical axis of each graph denotes the detected intensity.

As can be seen by comparing the waveform diagram on the generation side and the waveform diagram on the detection side, there is a high correlation in the change in the intensity of the terahertz wave between the generation side and the detection side. Therefore, it can be recognized that the generated terahertz wave is surely detected at each frequency. To actually measure the spectral information of the measurement sample, a method of measuring the terahertz waves when there is a measurement sample and when there is no measurement sample and comparing the measurement results to obtain the spectral information of the measurement sample is used. The wavelength of the terahertz wave may be switched and inputted to the measurement sample, and the measurement results obtained for several wavelengths may be compared to obtain the spectral information of the measurement sample.

Figure 18:
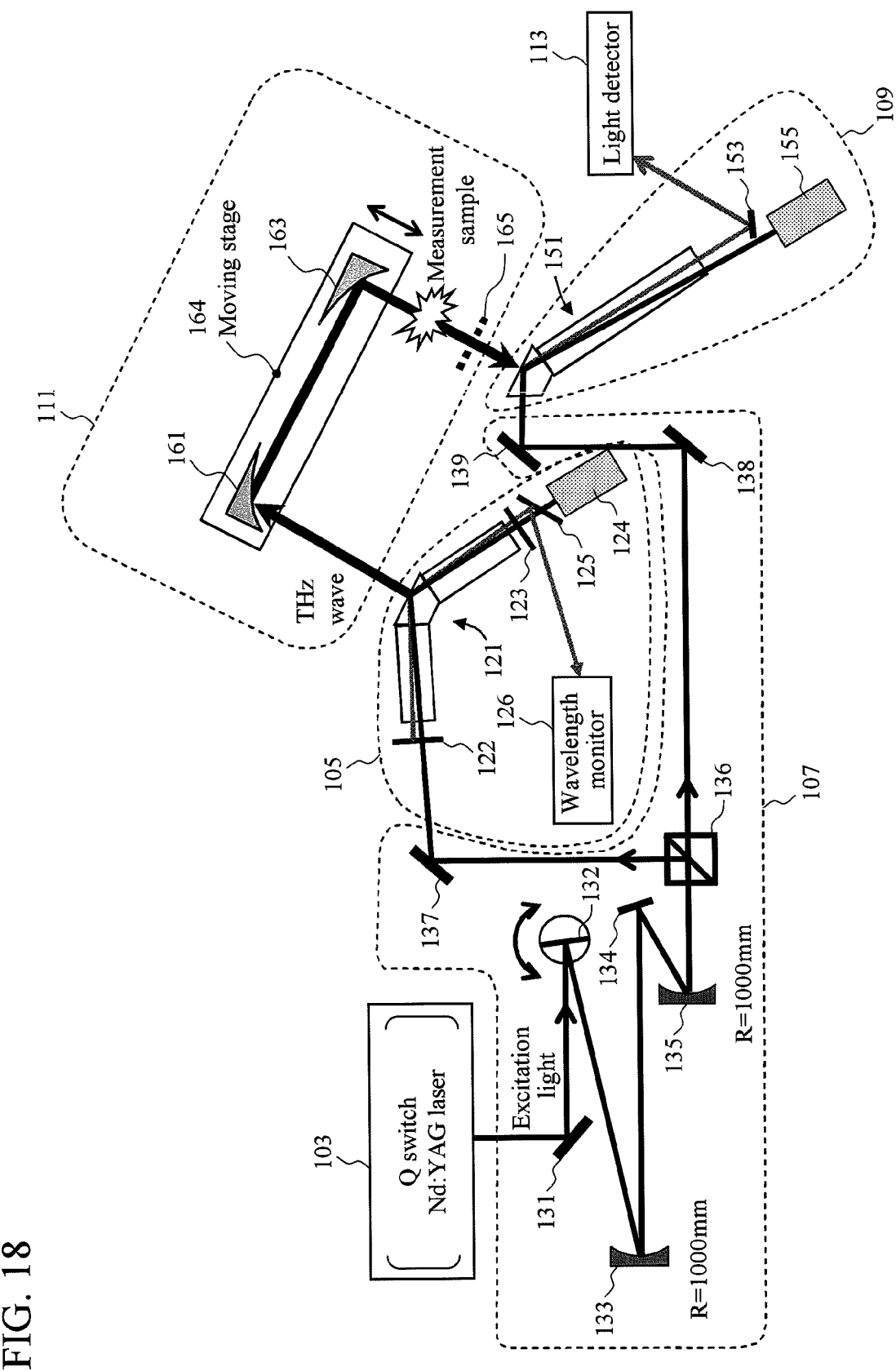
FIG. 18 is a diagram for explaining a drive mechanism of a terahertz wave phase control optical system.

(E) Drive Mechanism Suitable for Additional Installation to Terahertz Wave Generation/Detection System A drive mechanism suitable for additional installation to the terahertz wave generation/detection system will be described here. Specifically, a drive mechanism for position adjustment of the terahertz wave phase control optical system 111 will be described. FIG. 18 shows a conceptual configuration example of the terahertz wave generation/detection system with the drive mechanism.

The parts corresponding to FIG. 2 are designated with the same reference numerals in FIG. 18. The terahertz wave generation/detection system shown in FIG. 18 is different from the system shown in FIG. 2 in that two parabolic mirrors 161 and 162 constituting the terahertz wave phase control optical system 111 are mounted on a moving stage 164.

The two parabolic mirrors 161 and 162 are fixed to the moving stage 164. The input/output angles of the terahertz wave relative to the two parabolic mirrors 161 and 162 do not change in the moving stage 164 even during the movement, and the moving stage 164 is configured to change only the optical path length of the terahertz wave. More specifically, the angle phase matching conditions do not change before and after the movement of the moving stage 164, and only the optical path length (phase) of the terahertz wave changes.

For example, the moving stage 164 is configured to move along a guide not shown. The moving stage 164 is realized through a drive mechanism not shown (for example, motor and other drive systems). The moving stage 164 moves in a linear direction, and various known drive mechanisms can realize the movement. FIG. 18 shows moving directions of the moving stage 164 with arrows. The control apparatus 115 controls the movement of the moving stage 164.

Hereinafter, applications suitable when the terahertz wave phase control optical system 111 includes a mechanism capable of driving the optical path length in a variable manner will be described.

(E-1) Application 1

To measure the transmissivity, reflectivity, etc. of the measurement sample using the terahertz wave, amplitude information of the terahertz wave obtained by interaction with the measurement sample is usually acquired. However, other than the amplitude information, phase information may be important. For example, the phase information is required to obtain information of the refractive index, etc. of the measurement sample.

In this case, the terahertz wave generation/detection system including the moving stage 164 is effective. In the system configuration, the terahertz wave emitted from the wavelength variable terahertz wave source 105 is led to the terahertz wave phase control optical system 111 and then directed to the measurement sample. The nonlinear light conversion terahertz wave detector 109 measures the terahertz wave transmitted through the sample.

The terahertz wave phase control optical system 111 here is an optical system including the parabolic mirrors 161 and 163 arranged on the moving stage 164. The moving stage 164 moves parallel to the incidence direction of the terahertz wave emitted from the wavelength variable terahertz wave source 105 and parallel to the incidence direction of the terahertz wave to the nonlinear light conversion terahertz wave detector 109. The movement of the moving stage 164 changes the optical path length of the terahertz wave. Therefore, the phase of the terahertz wave can be controlled. The control apparatus 115 controls the movement (i.e. phase of terahertz wave entering the nonlinear light conversion terahertz wave detector 109) of the moving stage 164.

In this way, the amplitude waveform of the terahertz wave can be obtained by measuring the terahertz wave transmitted through or reflected from the measurement sample while moving the moving stage 164. The phase information of the terahertz wave related to the measurement sample can be acquired through the comparison of waveforms obtained when the moving stage 164 is moved within the same range before and after the insertion of the measurement sample.

(E-2) Application 2

Furthermore, the moving stage 164 can be used to optimize the detection conditions of the terahertz wave (specifically, to maximize the detected intensity of the near-infrared light (optical signal) detected by the light detector 113).

As described, the detection of the terahertz wave is realized by detecting the near-infrared light (optical signal) generated when the excitation light and the terahertz wave are mixed in the nonlinear optical crystal. The phase of the terahertz wave and the phase of the mixed excitation light need to match to increase the generated intensity of the near-infrared light. Therefore, to satisfy the optimal detection conditions, it is desirable if the control apparatus 115 that monitors the detected intensity of the light detector 113 controls the position (i.e. phase of terahertz wave entering the nonlinear light conversion terahertz wave detector 109) of the moving stage 164 to optimal conditions. The installation of the phase adjustment function allows highly sensitive measurement of the terahertz wave.

What is claimed is:

1. A monochromatic wavelength variable terahertz wave generation/detection system comprising:
   one excitation light source that generates excitation light of monochromatic wavelength;
   a wavelength variable terahertz wave source that inputs the excitation light to satisfy a first angle phase matching condition suitable to generate a terahertz wave and that generates the terahertz wave;
   a terahertz wave phase control optical system that leads the terahertz wave generated from the wavelength variable terahertz wave source to a measurement sample;
   a nonlinear light conversion terahertz wave detector that inputs the terahertz wave passed through the measurement sample and the excitation light to satisfy a second angle phase matching condition and that converts the wavelength of the inputted terahertz wave to form a light wave;
   a light detector that detects the light wave outputted from the nonlinear light conversion terahertz wave detector;
   an excitation light phase control optical system including, on a light path of the excitation light, an optical element capable of changing an incidence angle of the excitation light to a generation point of the terahertz wave in the wavelength variable terahertz wave source and an incidence angle of the excitation light to an incidence point of the terahertz wave in the nonlinear light conversion terahertz wave detector to set both the generation point and the incidence point at the same time on the focal points in a confocal optical system; and
   a control apparatus that controls at least one of the wavelength variable terahertz wave source, the terahertz wave phase control optical system, the nonlinear light conversion terahertz wave detector, the light detector, and the excitation light phase control optical system.

2. The monochromatic wavelength variable terahertz wave generation/detection system according to claim 1, wherein the excitation light phase control optical system is a confocal optical system that divides the excitation light outputted from the excitation light source into two, leads one of the excitation lights to the wavelength variable terahertz wave source, and leads the other excitation light to the nonlinear light conversion terahertz wave detector.

3. The monochromatic wavelength variable terahertz wave generation/detection system according to claim 1, wherein the excitation light phase control optical system is constituted by a first confocal optical system and a second confocal optical system, and
   the first confocal optical system leads the excitation light outputted from the excitation light source to the wavelength variable terahertz wave source, and the second confocal optical system leads the excitation light passed through the wavelength variable terahertz wave source to the nonlinear light conversion terahertz wave detector.

4. The monochromatic wavelength variable terahertz wave generation/detection system according to claim 1, wherein the optical element located on the light path of the excitation light in the excitation light phase control optical system is a mirror arranged on a galvano scanner.

5. The monochromatic wavelength variable terahertz wave generation/detection system according to claim 1, further comprising
   a drive mechanism that can change an optical path length of the terahertz wave in the terahertz wave phase control optical system while maintaining the second angle phase matching condition being satisfied, wherein
   the control apparatus performs variable control of the optical path length of the terahertz wave through the drive mechanism to maximize the detection output of the light wave obtained by the light detector.

6. The monochromatic wavelength variable terahertz wave generation/detection system according to claim 1, further comprising
   a drive mechanism that can change an optical path length of the terahertz wave in the terahertz wave phase control optical system while maintaining the second angle phase matching condition being satisfied, wherein
   the control apparatus performs variable control of the optical path length of the terahertz wave through the drive mechanism within a predetermined range during a measurement operation.

7. A monochromatic wavelength variable terahertz wave generation/detection method comprising:
   a first step of inputting excitation light of monochromatic wavelength outputted from one excitation light source to a wavelength variable terahertz wave source to satisfy a first angle phase matching condition suitable to generate a terahertz wave and generating the terahertz wave;
   a second process of leading the terahertz wave generated in the first process to a measurement sample through a terahertz wave phase control optical system;
   a third process of inputting, to the nonlinear light conversion terahertz wave detector, the terahertz wave passed through the measurement sample and the excitation light to satisfy a second angle phase matching condition and converting the wavelength of the inputted terahertz wave to form a light wave;
   a fourth process of detecting, by a light detector, the light wave generated in the third process; and
   a fifth process of simultaneously adjusting, through an optical element of an excitation light phase control optical system, an incidence angle of the excitation light to a generation point of the terahertz wave in the wavelength variable terahertz wave source and an incidence angle of the excitation light to an incidence point of the terahertz wave in the nonlinear light conversion terahertz wave detector to set both the generation point and the incidence point at the same time on the focal points in a confocal optical system.

8. The monochromatic wavelength variable terahertz wave generation/detection method according to claim 7, wherein
the excitation light phase control optical system divides the excitation light outputted from the excitation light source into two, leads one of the excitation lights to the wavelength variable terahertz wave source, and leads the other excitation light to the nonlinear light conversion terahertz wave detector.

9. The monochromatic wavelength variable terahertz wave generation/detection method according to claim 7, wherein
the excitation light phase control optical system is constituted by a first control optical system and a second control optical system, and
the first control optical system leads the excitation light outputted from the excitation light source to the wavelength variable terahertz wave source, and the second control optical system leads the excitation light passed through the terahertz wave parametric source to the nonlinear light conversion terahertz wave detector.

10. The monochromatic wavelength variable terahertz wave generation/detection method according to claim 7, further comprising
a process of performing variable control of an optical path length of the terahertz wave through a drive mechanism to maximize the detection output of the light wave obtained by the light detector when the drive mechanism that can change the optical path length of the terahertz wave in the terahertz wave phase control optical system while maintaining the second angle phase matching condition being satisfied is included.

11. The monochromatic wavelength variable terahertz wave generation/detection method according to claim 7, further comprising
a process of performing variable control of an optical path length of the terahertz wave through a drive mechanism within a predetermined range during a measurement operation when the drive mechanism that can change the optical path length of the terahertz wave in the terahertz wave phase control optical system while maintaining the second angle phase matching condition being satisfied is included.

* * * * *